United States Patent
Chang et al.

(10) Patent No.: US 7,015,038 B2
(45) Date of Patent: Mar. 21, 2006

(54) METHOD AND APPARATUS FOR PREPARING AND CULTURING CELLS

(75) Inventors: King-Ming Chang, Hsinchu (TW);
Ya-Chun Tseng, Jubei (TW);
Long-Shuenn Jean, Chiai (TW);
Benning Wang, Taipei (TW)

(73) Assignee: Industrial Technology Research Institute, (TW)

( * ) Notice: Subject to any disclaimer, the term of this patent is extended or adjusted under 35 U.S.C. 154(b) by 353 days.

(21) Appl. No.: 10/157,543

(22) Filed: May 28, 2002

(65) Prior Publication Data

US 2003/0093034 A1 May 15, 2003

(30) Foreign Application Priority Data

Nov. 9, 2001 (TW) .............................. 90127901 A

(51) Int. Cl.
*C12N 5/00* (2006.01)
*C12M 3/04* (2006.01)

(52) U.S. Cl. ...................... 435/395; 435/399; 435/402; 435/286.5; 435/299.1; 435/299.2; 435/818

(58) Field of Classification Search ................ 435/3, 435/395, 398, 389, 402, 286.5, 286.6, 293.1, 435/294.1, 299.1, 299.2, 304.1, 304.2, 309.1, 435/818

See application file for complete search history.

(56) References Cited

U.S. PATENT DOCUMENTS

| 4,065,360 A | * | 12/1977 | Kreb, III | ..................... 600/578 |
| 6,323,022 B1 | * | 11/2001 | Chang et al. | ............. 435/286.5 |
| 2003/0143727 A1 | * | 7/2003 | Chang | ..................... 435/289.1 |

FOREIGN PATENT DOCUMENTS

| DE | 3607582 A | * | 9/1987 |
| JP | 2000262269 A | * | 9/2000 |
| SU | 734281 B | * | 5/1980 |
| SU | 1131899 A | * | 12/1984 |
| WO | WO 9923243 A1 | * | 5/1999 |

* cited by examiner

Primary Examiner—William H. Beisner
(74) Attorney, Agent, or Firm—Merchant & Gould P.C.

(57) ABSTRACT

A method and an apparatus for preparing and culturing cells, particularly bone marrow stromal cells. The method includes the steps of placing an oxygenator and a scaffold in a container, such as a syringe, withdrawing bone marrow stromal cells with the syringe, evenly distributing the cells on the scaffold, connecting the syringe with a reservoir with a medium to enrich the syringe with the medium, and promoting the medium level movement in the syringe to culture bone marrow stromal cells.

26 Claims, 13 Drawing Sheets

METHOD AND APPARATUS FOR PREPARING AND CULTURING CELLS

BACKGROUND OF THE INVENTION

1. Field of the Invention

The present invention relates to a method and an apparatus for preparing and culturing cells. More particularly, the present invention relates to a method and an apparatus for preparing and culturing bone marrow stromal cells.

2. Description of the Related Arts

In general, petri dishes are used for preparing bone marrow stromal cells. For example, the U.S. Pat. No. 5,942,225 discloses a method for preparing bone marrow stromal cells, comprising the steps of withdrawing bone marrow with a syringe, adding a medium and Percoll gradient, moving the part of mononuclear cells to a petri dish after centrifugation, replacing the medium after three days cultivation, removing impurities based on the attachment feature of stromal cells, and transferring stromal cells to another petri dish with a porous scaffold to continue culturing while achieving a certain amount of cells.

However, the method mentioned above includes several transfer steps during the cultivation which increases the possibility of contamination and cell loss. In addition, the method of placing a scaffold in a petri dish has a risk of losing cells in the petri dish that fail to attach to the scaffold. In other words, the efficiency for cell attachment is low leading to a lower utility of cells. Even if cells stay on the scaffold, they tend to sink to the base of the scaffold, resulting in an uneven distribution. Therefore, there is still a need for a solution to culture bone marrow stromal cells and it is the primary object of the present invention.

SUMMARY OF THE INVENTION

The present invention provides a simple and effective method and an apparatus for preparing and culturing bone marrow stromal cells. The method and apparatus for preparing and culturing bone marrow stromal cells in the present invention comprise the steps of placing an oxygenator and a scaffold in a container, such as a syringe, withdrawing bone marrow stromal cells with the syringe, distributing the cells evenly on the scaffold, connecting the syringe with a reservoir of a medium to enrich the syringe with the medium, and promoting the medium level movement in the syringe to culture bone marrow stromal cells. Since the oxygenator is composed of porous materials, when the medium level is driven down and the oxygenator is exposed to the air, liquid film forms on the pores of the porous oxygenator due to surface tension and this broadens surface area for aeration. When the medium level is driven up and the oxygenator is covered by the medium, the oxygen in the liquid films is taken by the medium. Therefore, the medium level movement mentioned above fully supplies the oxygen needed for culturing bone marrow stromal cells.

The method and the apparatus in the present invention effectively withdraws bone marrow stromal cells into the scaffold for cultivation, and thus enhances the attachment of bone marrow stromal cells. The syringe used for cultivation reduces contamination because it is unnecessary to transfer the scaffold into the other culture system. Hence, the quality of bone marrow stromal cells is maintained. The cultured tissue is then implanted at the site in order to repair the damaged tissue.

BRIEF DESCRIPTION OF THE DRAWINGS

The patent or application file contains at least one drawing executed in color. Copies of this patent or application publication with color drawing(s) will be provided by the Office upon request and payment of the necessary fee.

The present invention will be more fully understood and further advantages will become apparent when reference is made to the following description of the invention and the accompanying drawings in which.

DETAILED DESCRIPTION OF THE INVENTION

Figure 1:
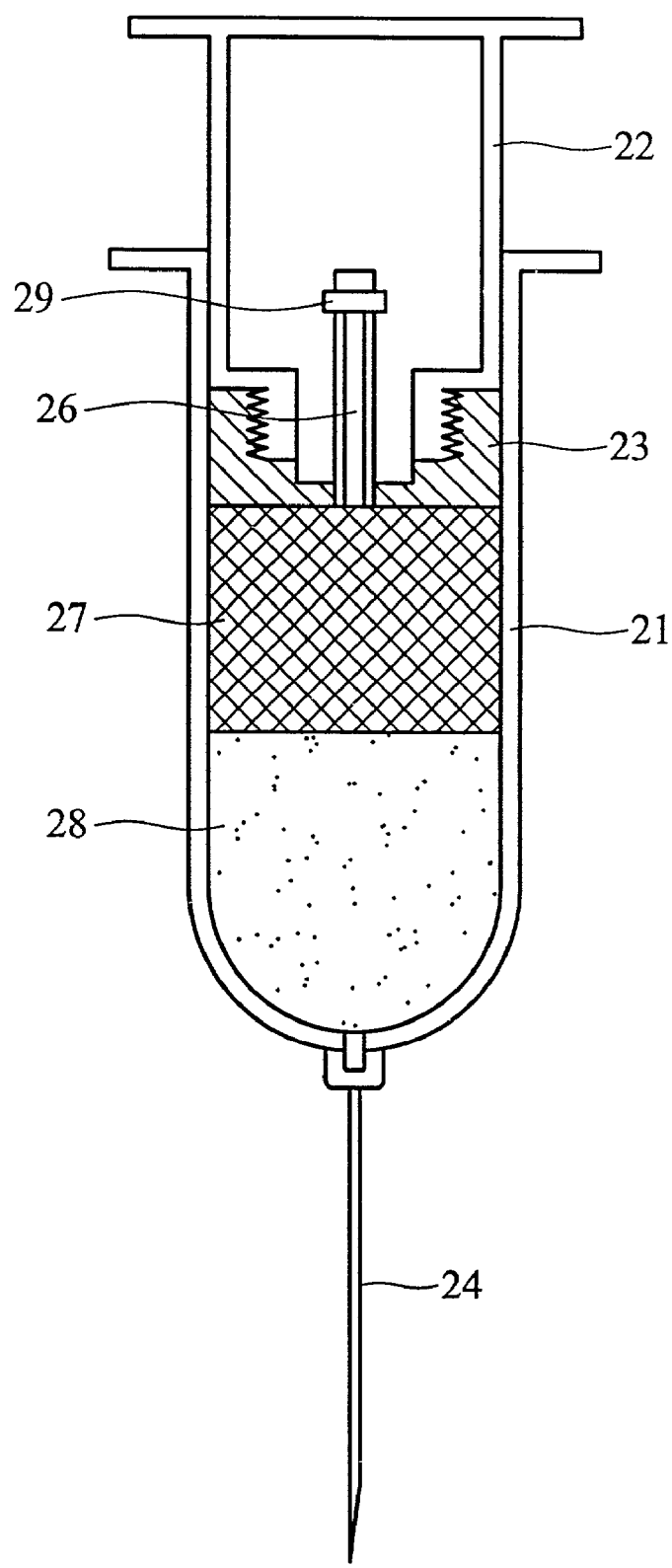
FIG. 1 is a schematic diagram showing an apparatus for preparing bone marrow stromal cells in the present invention.

In accordance with the present invention, there is provided a method and apparatus for preparing and culturing bone marrow stromal cells.

The apparatus for preparing bone marrow cells in the present invention includes a syringe, a needle connected to the base of the syringe, a push rod inside the syringe, a piston connected to the base of the push rod with thread, an oxygenator inside the syringe, a scaffold underneath the oxygenator inside the syringe. A ventilator is sited on the piston, hidden in the push rod, and connected to the internal part of the syringe. An air filter is sited on the entrance of the ventilator for filtering microbes out.

The oxygenator is composed of porous materials for aeration. The scaffold provided for cell attachment is composed of porous biomedical materials, biodegradable porous high-molecular materials, ceramics, fibers, non-woven or woven sheets. The materials are collagen or its copolymers, ceramics, PLGA, PP, PS, PET, hydrophilic polyurethane, polyester, polyvinyl acetate blends, polyvinylidene chloride, polybutadiene, polyfluorocarbons and the like.

The apparatus for preparing bone marrow stromal cells is used for withdrawing bone marrow until the scaffold is filled up. After that, the push rod is rotated to separate from the piston, and the needle is then removed in order to connect the syringe with a reservoir. This syringe becomes an apparatus for culturing bone marrow stromal cells. The ventilator is switched on to ventilate the air. Air is pressed into a ventilator of the reservoir in order to drive the medium into the syringe, and bone marrow mixed with the medium is cultured in the incubator in 37° C. with 5% $CO_2$ for several hours or several days.

The syringe is sited on a holder which includes a track, and the syringe is promoted up and down by a step motor for dynamic cultivation: When the syringe is driven up, it is obvious that the medium level of the syringe is driven down and the oxygenator is exposed to the air according to the principle of "connected vessels". Since the oxygenator is composed of porous materials, the liquid film forms on the pores and this increases surface area for aeration, and thus, more oxygen is absorbed into the liquid films. When the syringe is driven down, the oxygenator is covered by the medium and the oxygen inside the oxygenator is received by the medium. Such up-and-down movement of medium level supplies enough oxygen for cell cultivation.

Accordingly, the possibility of contamination or cell loss is lowered by utilizing aspiration syringe as a tool for cultivation since the times for transferring cells are reduced. In addition, the probability of cell attachment and even distribution of cells is improved using vacuum pressure to withdraw cells into the scaffold because this enhances cells' entry into the pores of the scaffold.

The step motor mentioned above can be replaced by different power plants, such as hydraulic cylinder or air cylinder, to promote the up-and-down movement of the syringe in order to change the medium level.

The other embodiment of the apparatus for preparing cells comprises two or more syringes connected to one needle which enhances the amount of cells for cultivation.

Another embodiment of the apparatus for preparing cells comprises the syringe fully filled by the scaffold rather than the porous oxygenator. The scaffold itself is also used as the oxygenator while the medium level is moved up and down.

Furthermore, the up-and-down movement of the medium level can be modified. Two sensors are sited beside the syringe, and in the other side, the ventilator of the reservoir is connected to an air pump through a solenoid valve. A controller is connected among the solenoid valve and the sensors. When the sensors detect a downward medium level, the controller promotes the opening or closing of valves. The air pressure produced by the air pump then enters the reservoir through the valves of the solenoid valve and the ventilator in order to drive the medium level of the reservoir flowing downward and enter the syringe. When the sensors detect an upward medium level, the controller promotes the opening or closing of the valves and the medium level of the syringe flows downward. The air in the reservoir is evacuated through the ventilator and the solenoid valve. As a result, the medium level of the syringe is driven up and down.

Another embodiment of the device for liquid driving in the present invention is that the controller includes a timer and the time interval for achieving a liquid level in the syringe can be calculated. When the time interval is reached, the controller switches the opening or closing of the valves. In a word, this arrangement results in the up-and-down movement of the medium level inside the syringe.

Moreover, the apparatus for preparing cells in the present invention is used not only for culturing bone marrow stromal cells, but also for culturing other stromal cells, hematopoietic cells, chondrocytes, osteoblasts, epithelial cells, mesenchymal cells, endothelial cells, cell lines, other primary cells, etc. The method of preparing these cells comprises the steps of culturing cells in a petri dish, detaching the cells and adding a medium, withdrawing the mixture of the cells and the medium into the apparatus in the present invention, and culturing the cells to obtain a in vitro tissue.

Without intending to limit it in any manner, the present invention will be further illustrated by the following examples.

EXAMPLE

Example I is the description of the method and the apparatus for preparing and culturing cells in the present invention, and Example II and III are animal tests performed by the method and the apparatus of this invention.

Example I

The Structure and the Application of the Apparatus for Preparing and Culturing Cells in the Present Invention In FIG. 1, the apparatus for preparing bone marrow cells in the present invention includes a syringe 21, a needle 24 connected to the base of the syringe 21, a push rod 22 inside the syringe 21, a piston 23 connected to the base of the push rod 22 with thread, an oxygenator 27 inside the syringe 21, a scaffold underneath the oxygenator 27 inside the syringe 21. A ventilator 26 is sited on the piston 23, hidden in the push rod 22, and connected to the internal part of the syringe 21. An air filter 29 is sited on the entrance of the ventilator 26 for filtering microbes out.

The oxygenator 27 is composed of porous materials for aeration. The scaffold 28 provided for cell attachment is composed of porous biomedical materials, biodegradable porous high-molecular materials, ceramics, fibers, non-woven or woven sheets. The materials are collagen or its copolymers, ceramics, PLGA, PP, PS, PET, hydrophilic polyurethane, polyester, polyvinyl acetate blends, polyvinylidene chloride, polybutadiene, polyfluorocarbons and the like.

Figure 2:
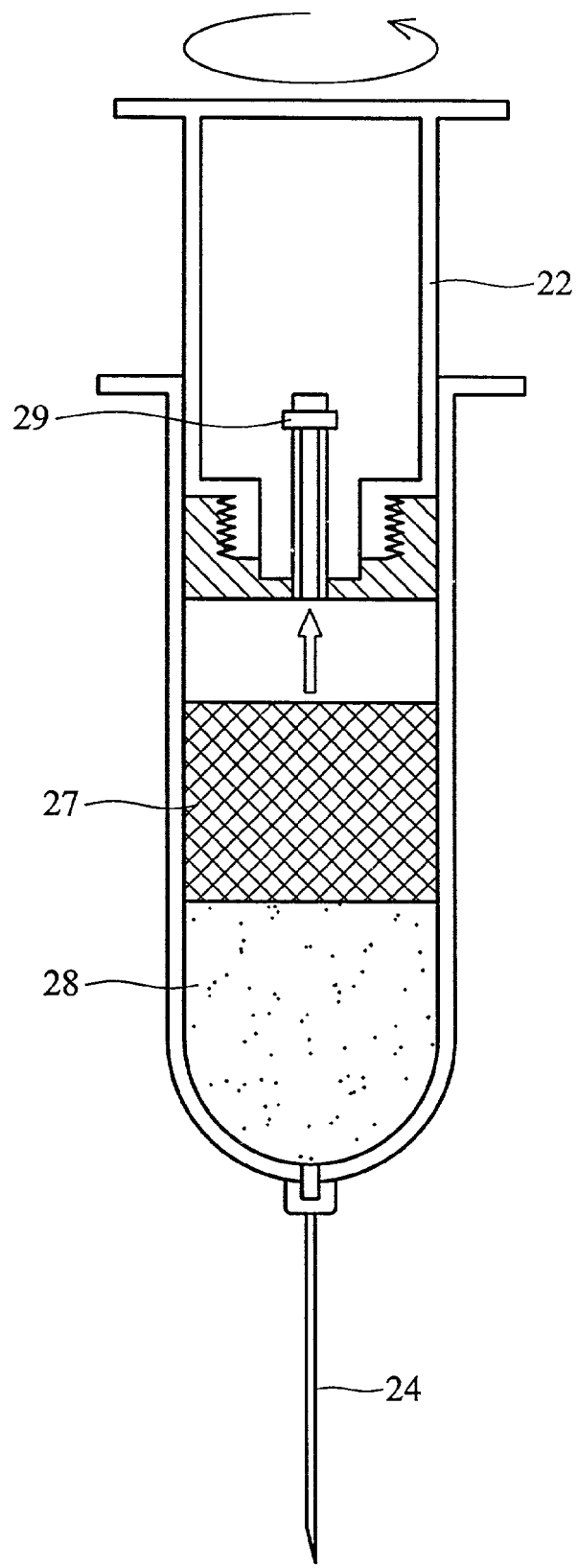
FIG. 2 is a diagram showing the status of withdrawing bone marrow with an apparatus for preparing bone marrow stromal cells.
Figure 3:
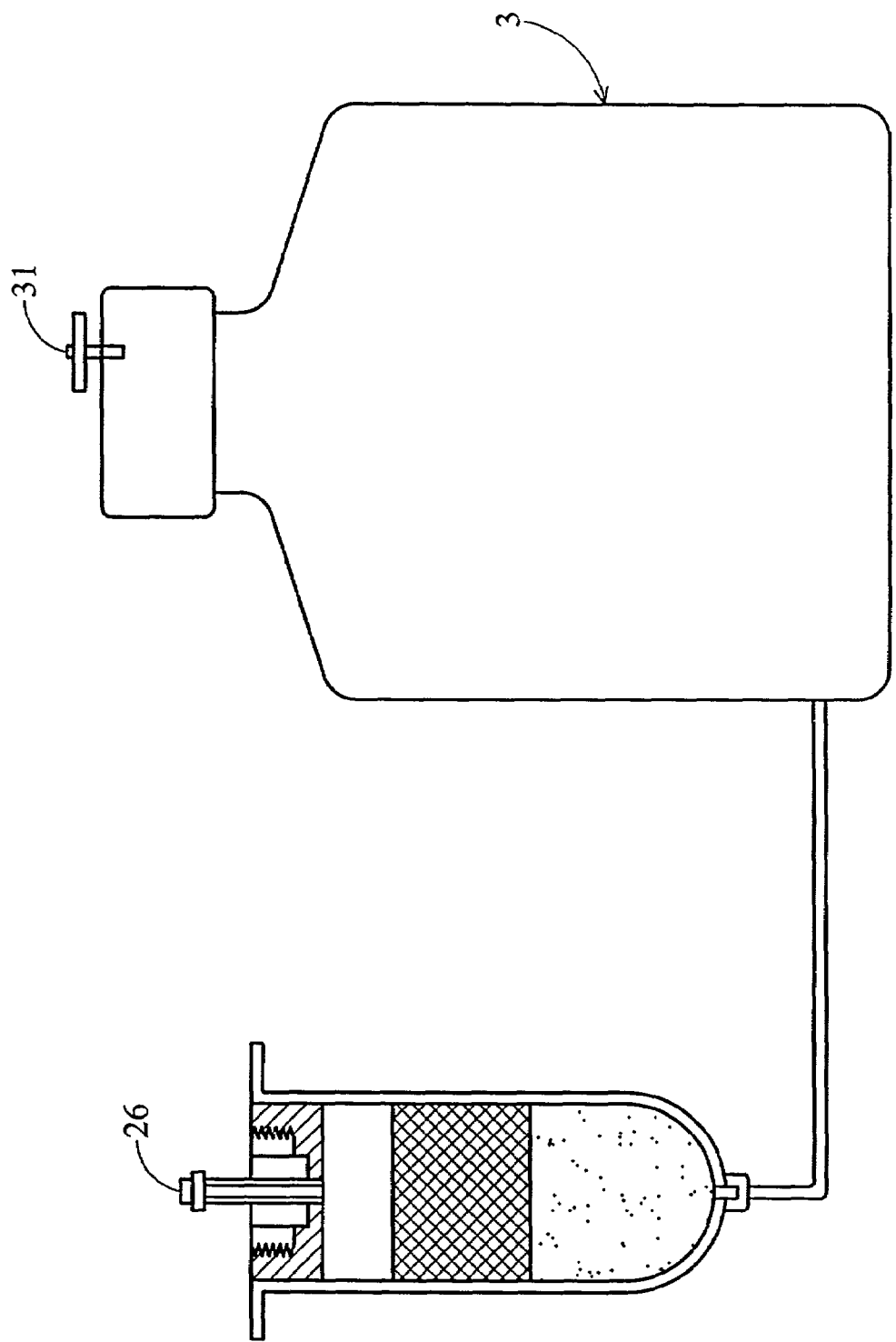
FIG. 3 is a schematic diagram showing an apparatus for culturing bone marrow stromal cells in the present invention.

The apparatus for preparing bone marrow stromal cells is used for withdrawing bone marrow until the scaffold 28 is filled up. In FIG. 2, the push rod 22 is rotated to separate from the piston 23, and the needle 24 is then removed in order to connect the syringe 21 with a reservoir 3 as shown in FIG. 3. This syringe becomes an apparatus for culturing bone marrow stromal cells. The ventilator 26 is switched on to ventilate the air. Air is pressed into a ventilator 31 of the reservoir 3 in order to introduce the medium into the syringe 21, and bone marrow mixed with the medium is cultured in the incubator in 37° C. with 5% $CO_2$ for several hours or several days.

Figure 4:
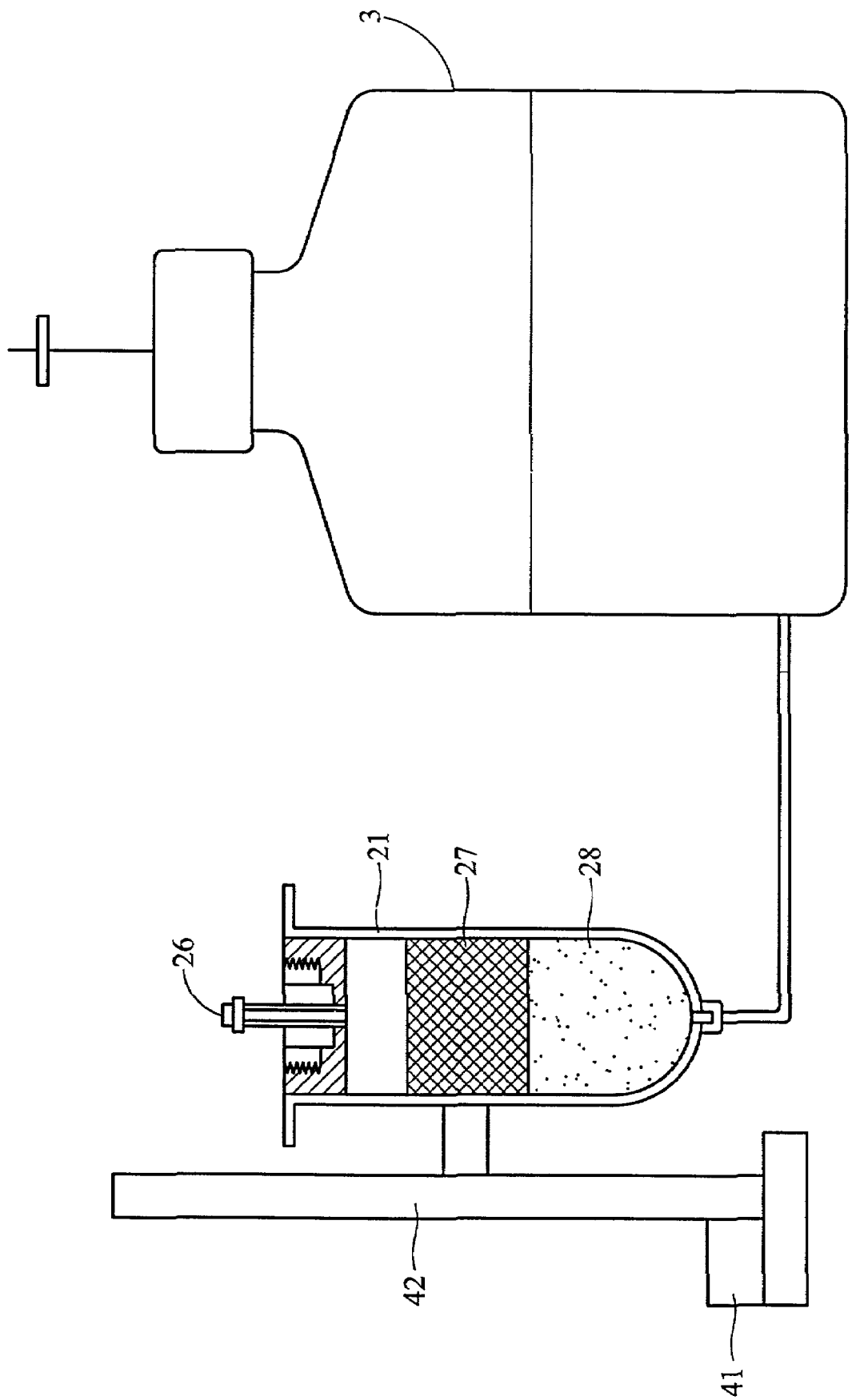
FIG. 4 is a diagram showing an example of the apparatus for culturing bone marrow stromal cells in the present invention connecting with a device for liquid driving.

In FIG. 4, the syringe 21 is sited on a holder 42 which includes a track, and the syringe 21 is promoted up and down by a step motor 41 for dynamic cultivation: When the syringe 21 is driven up, it is obvious that the medium level of the syringe 21 is driven down and the oxygenator 27 is exposed to the air according to the principle of "connected vessels". Since the oxygenator 27 is composed of porous materials, the liquid film forms on the pores and this increases surface area for aeration, and thus, more oxygen is solved into the liquid films. When the syringe 21 is driven down, the oxygenator 27 is covered by the medium and the oxygen inside the oxygenator 27 is received by the medium. Such up-and-down movement of medium level supplies enough oxygen for cell cultivation.

Accordingly, the possibility of contamination or cell loss is lowered by utilizing aspiration syringe as a tool for cultivation since the times of transferring cells are reduced. In addition, the probability of cell attachment and even distribution of cells is improved by using vacuum pressure to withdraw cells into the scaffold because this enhances cells' entry into the pores of the scaffold.

The step motor mentioned above can be replaced by different power plants, such as hydraulic cylinder or air cylinder, to promote the up-and-down movement of the syringe in order to change the medium level.

Figure 5:
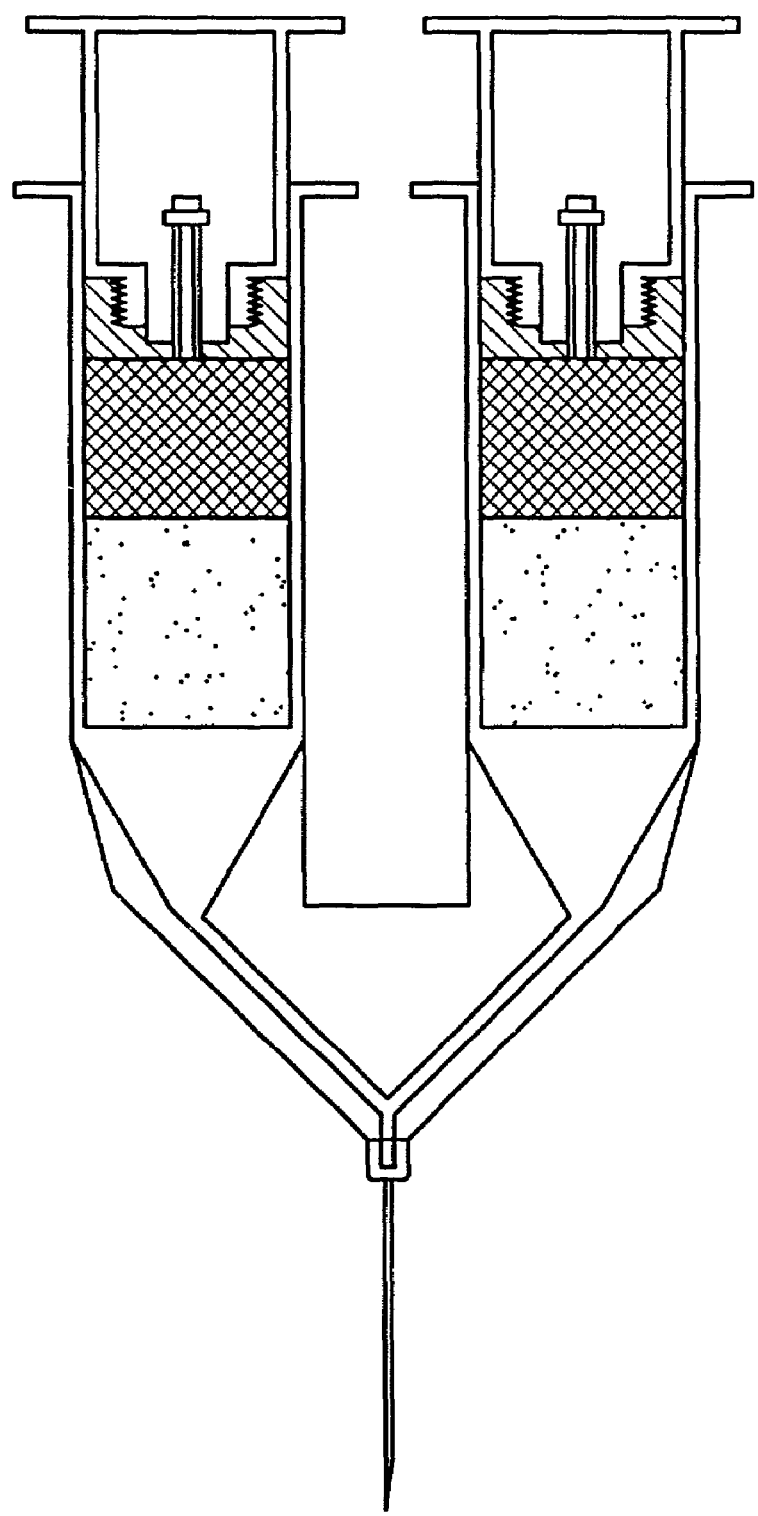
FIG. 5 is a diagram showing an example of the apparatus for preparing cells in the present invention.
Figure 6:
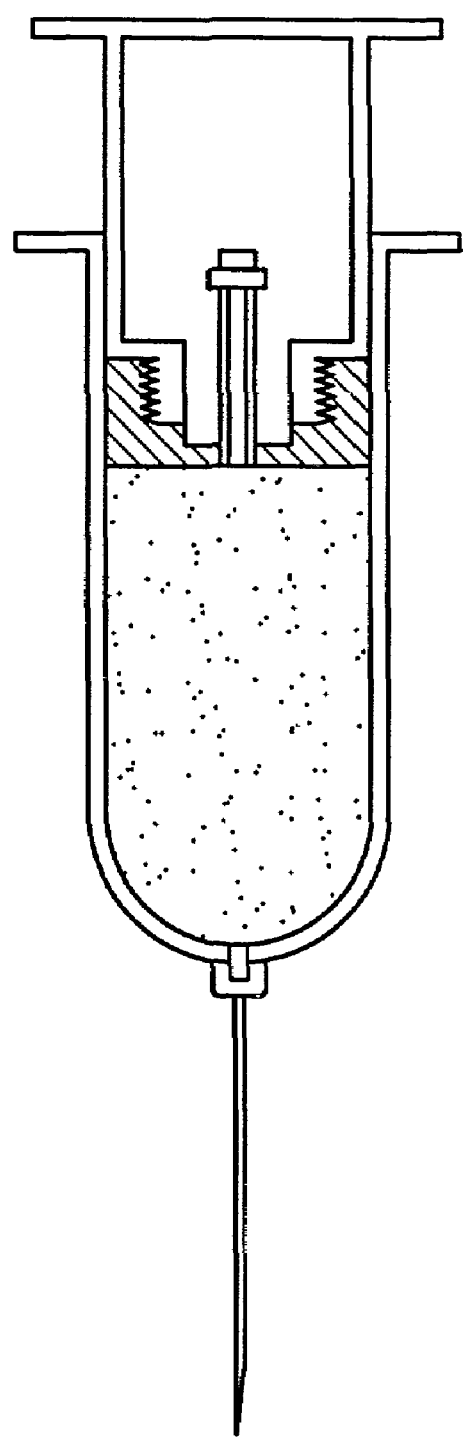
FIG. 6 is a diagram showing another example of the apparatus for preparing cells in the present invention.

The apparatus for preparing cells can also be modified. As shown in FIG. 5, two or more syringes are connected to one needle, and this enhances the amount of cells for cultivation. An additional modification is shown in FIG. 6, in which the syringe is filled by the scaffold rather than the porous oxygenator. The scaffold itself is also used as the oxygenator while the medium level is moved up and down.

Figure 7:
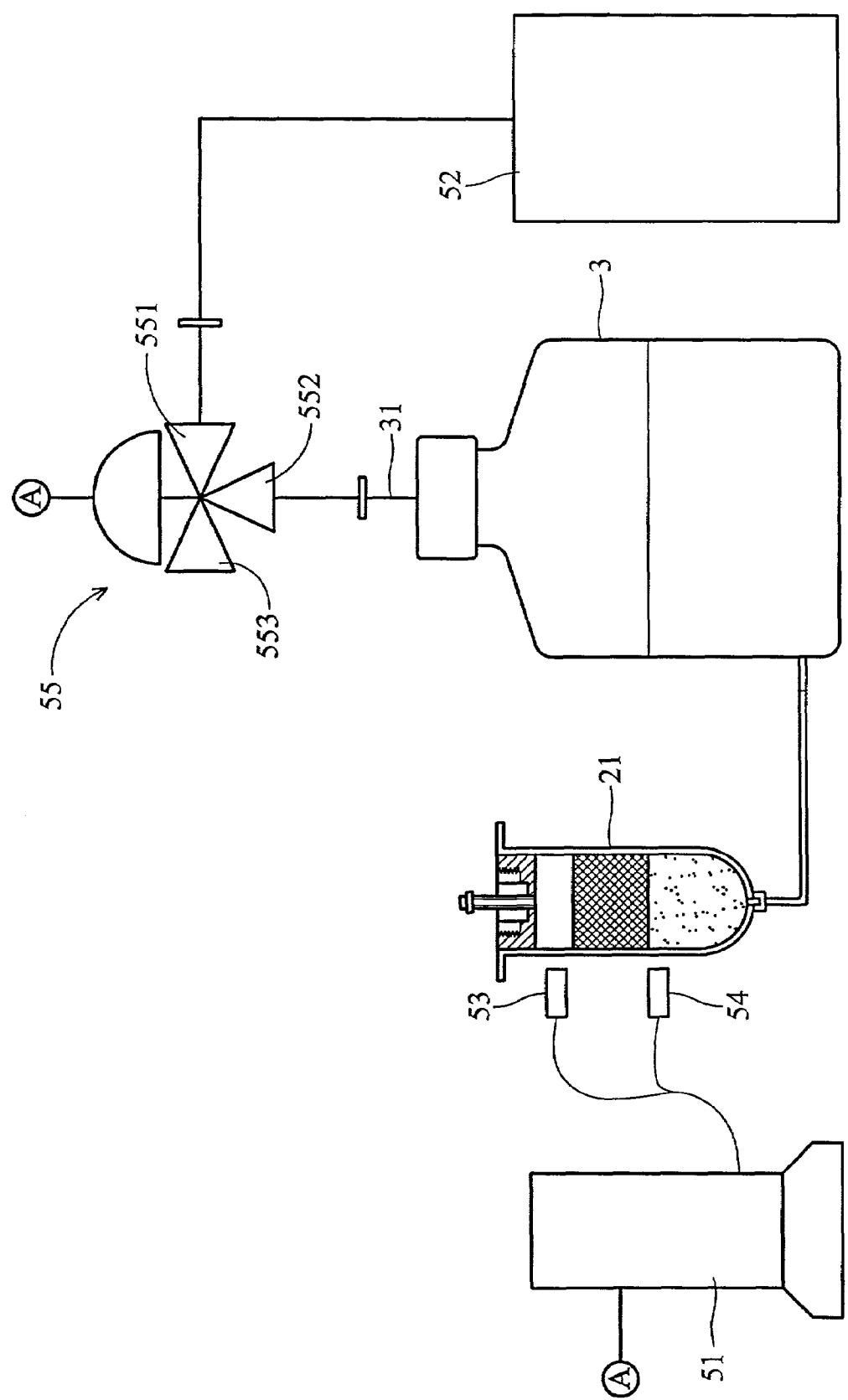
FIG. 7 is a diagram showing an example of the device for liquid driving in the present invention.

Furthermore, the up-and-down movement of medium level can be modified as shown in FIG. 7. In one side, two sensors 53 & 54 are sited beside the syringe 21, and in the other side, the ventilator 31 of the reservoir 3 is connected to an air pump 52 through a solenoid valve 55. A controller 51 is connected among the solenoid valve 55 and the sensors 53 & 54. When the sensors 53 & 54 detect a downward medium level, the controller 51 promotes the valve 552 opening and the valve 553 closing. The air pressure produced by the air pump 52 then enters the reservoir 3 through the valves 551 & 552 of the solenoid valve and the ventilator 31 in order to drive the medium level of the reservoir 3 downward and enter the syringe 21. When the sensors 53 & 54 detect an upward medium level, the controller 51 promotes the valve 553 opening and the valve 551 closing and the medium level of the syringe 21 flows downward. The air in the reservoir 3 is evacuated through the ventilator 31 and the valves 552 & 553 of the solenoid valve. As a result, the medium level of the syringe 21 is driven up and down.

Figure 8:
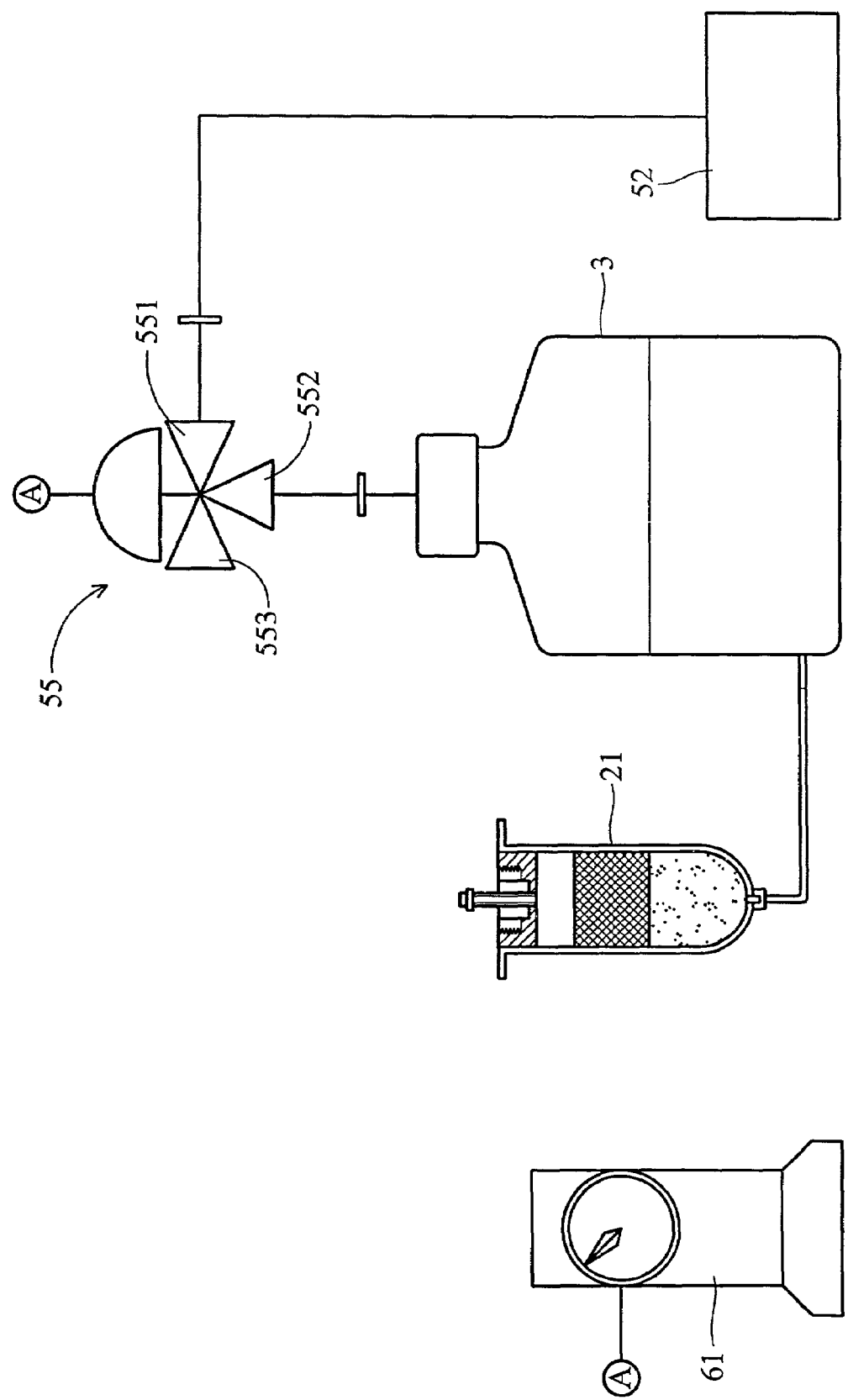
FIG. 8 is a diagram showing another example of the device for liquid driving in the present invention.

FIG. 8 is a diagram showing another example of the device for liquid driving in the present invention. In this example the controller 61 includes a timer and the time interval for achieving a liquid level in the syringe 21 can be calculated. When the time interval is reached, the controller 61 switches the opening or closing of the valves 551, 552, & 553, in the same manner of it in FIG. 7. In a word, this arrangement results in the up-and-down movement of the medium level inside the syringe 21.

Moreover, the apparatus for preparing cells in the present invention is used not only for culturing bone marrow stromal cells, but also for culturing other stromal cells, hematopoietic cells, chondrocytes, osteoblasts, epithelial cells, mesenchymal cells, endothelial cells, cell lines, other primary cells, etc. The method of preparing these cells comprises the steps of culturing cells in a petri dish, detaching the cells and adding a medium, withdrawing the mixture of the cells and the medium into the apparatus in the present invention, and culturing the cells to obtain a in vitro tissue.

Example II

In vitro Test for Preparing and Culturing Bone Marrow Stromal Cells

A New Zealand white (NZW) rabbit was anesthetized by IM anesthetics, the hair in hips area of the rabbit was removed and the hips of the rabbit are anesthetized by topical anesthetics. A 18 G needle was pricked into the ilium of the rabbit and the bone marrow was withdrawn from the ilium by the apparatus in the present invention. When 5 ml of bone marrow was withdrawn, the needle was removed and the syringe was connected to a reservoir. 5 ml of medium (low glucose-DMEM+10% fetal calf serum+antibiotics) was introduced into the syringe and the connected syringe and reservoir were placed in a 37° C. incubator with 5% $CO_2$ for 2 days.

Figure 9A:
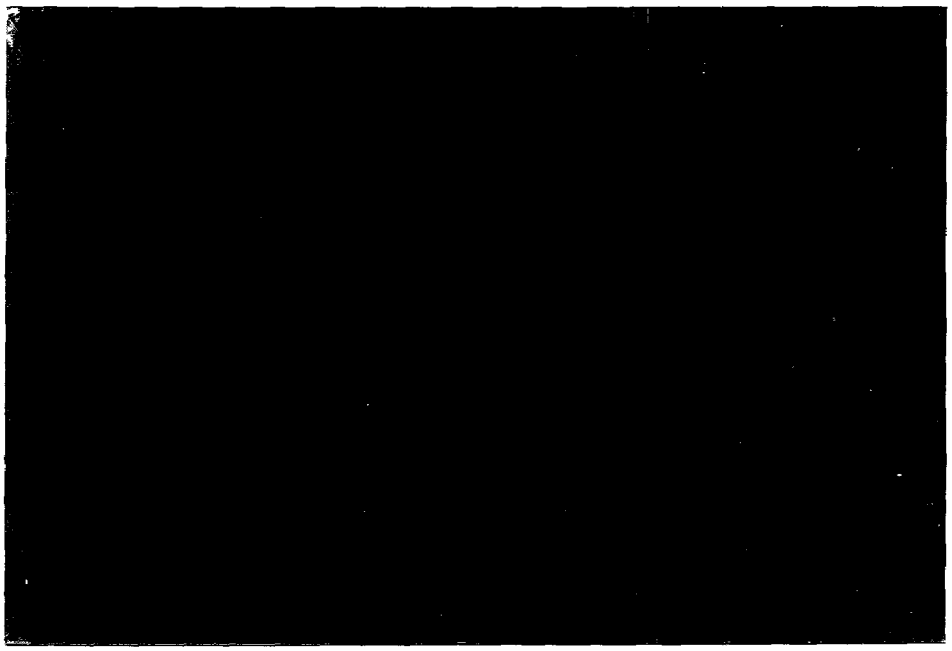
FIG. 9 shows microscopic photographs showing the status of cell growth in (a) a non-woven scaffold or a porous hydroxy-phosphorite scaffold which then were placed in a petri dish (b) or a bioreactor (c).
Figure 9A:
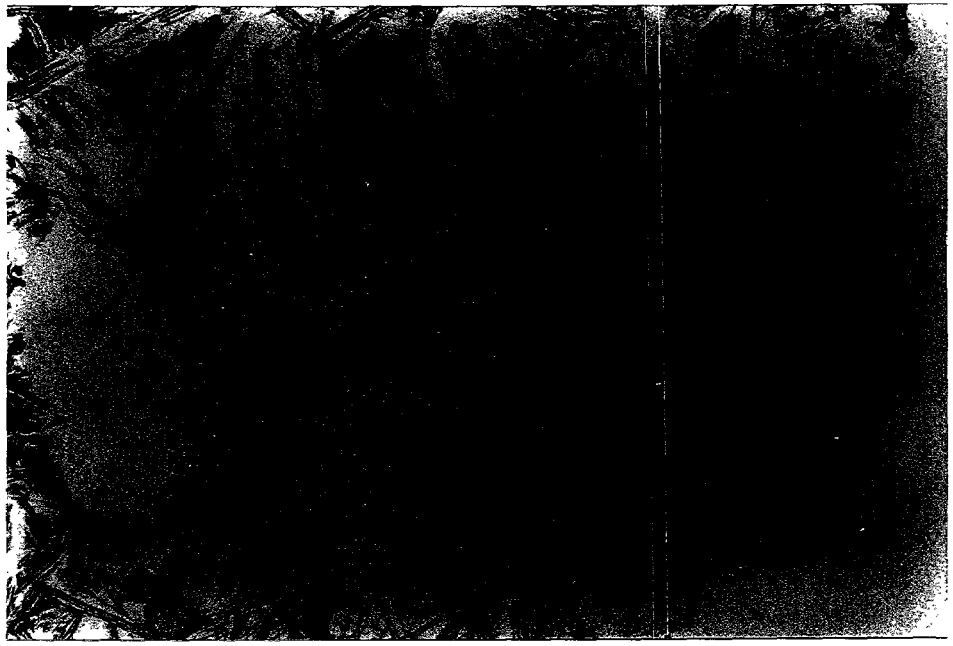
Figure 9B:
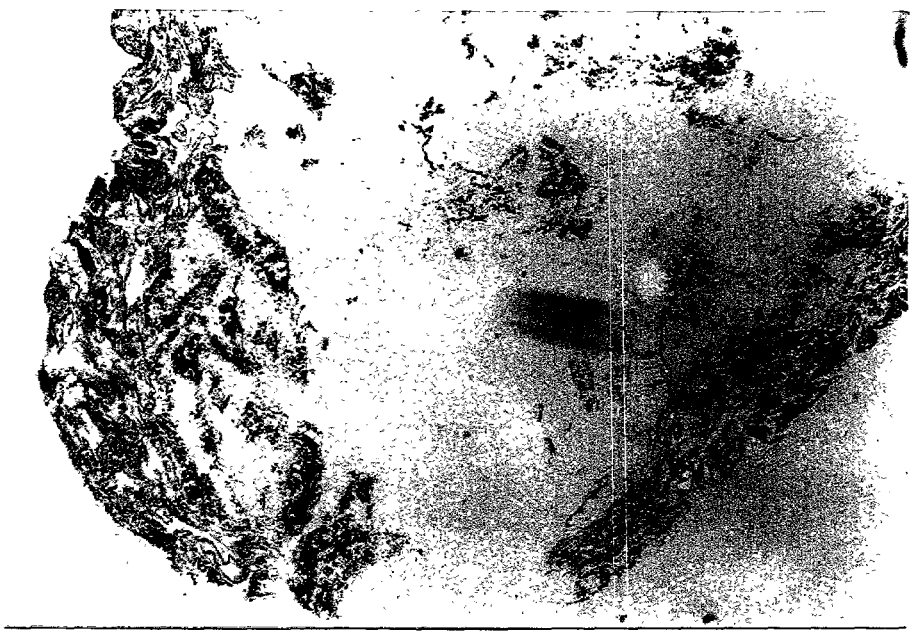
Figure 9C:
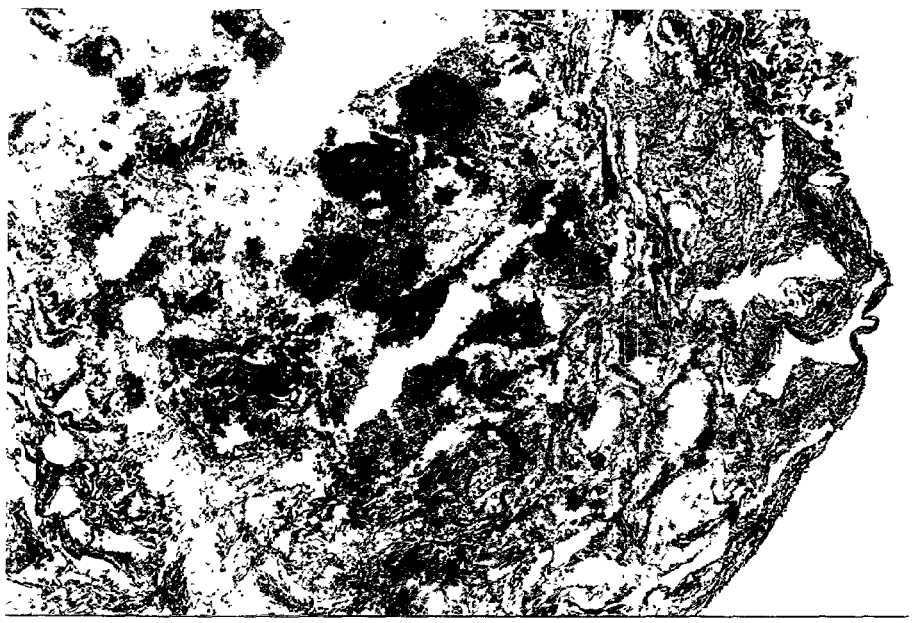
Figure 10:
FIG. 10 is a microscopic photograph showing the crystal violet staining result of cells cultured in the non-woven scaffold which then was placed in the bioreactor for 1 month.
Figure 11:
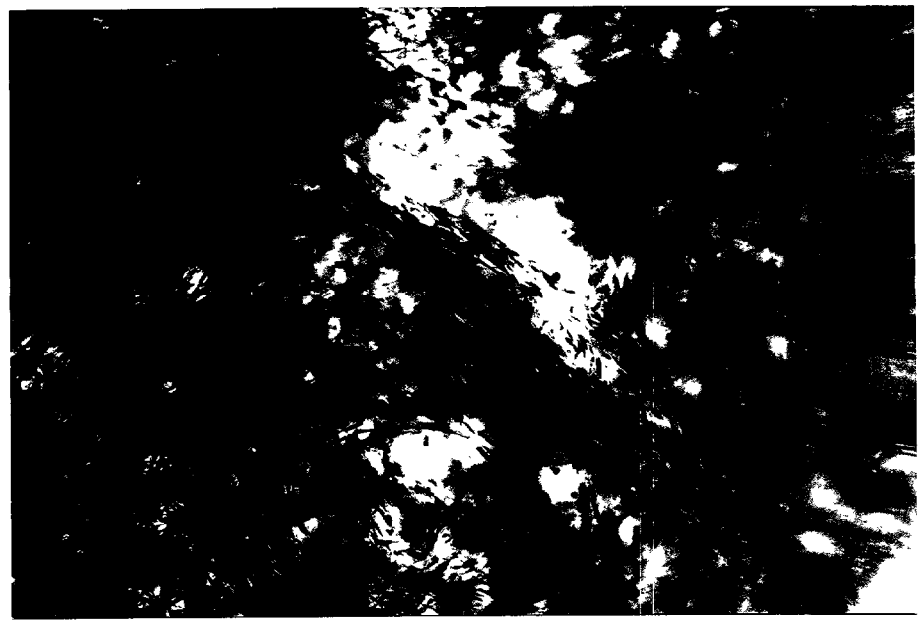
FIG. 11 is a microscopic photograph showing the MTT assay result of cells cultured in the non-woven scaffold which then was placed in the bioreactor for 1 month.
Figure 12:
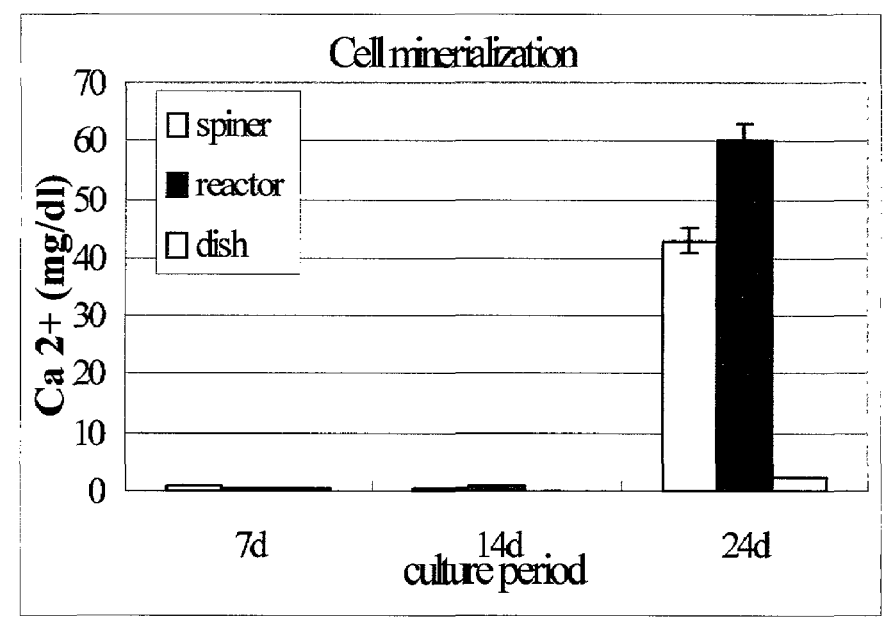
FIG. 12 is a bar chart showing the calcium content of the cultured cells in the non-woven scaffold which was then placed in the bioreactor for 1 month and induced mineralization.
Figure 13:
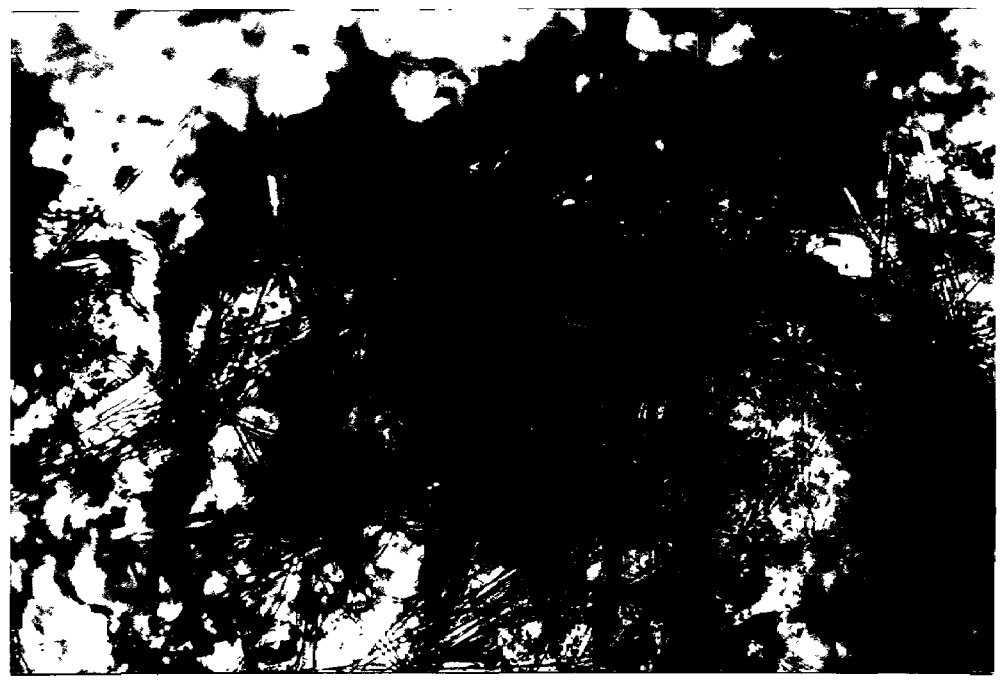
FIG. 13 is a microscopic photograph showing the Von Kossa's staining result of cells cultured in the non-woven scaffold which was then placed in the bioreactor for 1 month.

After 2 days cultivation, the syringe and the reservoir were connected to a device for liquid driving to move the liquid level up and down, and the bone marrow mixture was thus mixed with fresh medium. After one week, half of the medium was replaced with an osteanagenesis-inducing medium (low glucose-DMEM+10% fetal calf serum+antibiotics+ 10 mM β-glycerophosphate+50 μg/ml ascorbic acid+10 nM Dexamethasone), and the metabolites were then assayed. Half of the medium was refreshed every week. At the end of one month, the scaffold was assayed by cell counting, staining, and cell mineralization. The results are shown in FIG. 9-13. In FIG. 9a, cells were grown in a non-woven scaffold and then cultured in a bioreactor for one month. The H&E staining result confirms that cells attached on the scaffold and showed that cells proliferated and covered the scaffold. In FIGS. 9b & c, cells were grown in porous hydroxy-phosphorite scaffolds and then cultured in a petri dish (9b) and a bioreator (9c) for one month. The H&E staining results show that the cells cultured in the petri dish only grew on the surface of the scaffold, however, the cells cultured in the bioreactor grew all over the scaffold. That is, cells cultured by the method of the present invention have higher cell number and cell density than those cultured in the petri dish. FIG. 10-13 are photographs in microscopy showing the crystal violet staining result (10), the MTT assay result (11) and the Von Kossa staining result (13) of cells grown in the non-woven scaffold and then cultured in the bioreactor for 1 month. The Crystal violet staining result and the MTT assay result confirm that cell attached on the scaffold, and the Von Kossa staining result shows that the cells were minerialized. In FIG. 12, the calcium content of the cells cultured in the non-woven scaffold of the bioreactor for 1 month and then induced mineralization was increased.

Example III

In Vivo Test of Implantation

After one month culturing in the petri dish and the bioreactor separately, the scaffolds were stored in fresh medium for self-implantation. 3-month-old NZW rabbits were used.

The rabbits were anesthetized with a dosage of 2 ml of a 1:1 mixture of Ketamine (0.4 ml/kg; 健惠) and Combelen (0.4 ml/kg; Bayer) by IM. After the rabbits were unconscious, the hair on the femur was shaved and the predetermined surgery area of the rabbits was sterilized with tincture of iodine. The soft tissue covering the hind leg was carved about 5 cm deep, the muscle tissues covering the femurs were peeled off and an extension apparatus was used for support. A hole was drilled of a diameter of 10 mm and a depth of 5 mm in the femur. The implantation area, the hole, was washed by saline and the residue of bone fragments was removed. The scaffold with bone marrow stromal cells was implanted into the hole. Finally, the muscle and the outer skin were sutured layer by layer. The right leg of the rabbit was implanted with the scaffold cultured in the bioreactor, and the left leg was implanted with the scaffold cultured in the petri dish. The other rabbit was implanted with a scaffold without any cells as a control.

After three months, the rabbits were sacrificed, and their femurs were washed with PBS and fixed in 3.7% formaldehyde solution. After one week, the tissues were dehydrated with 50%, 70%, 80%, 90% and 100% ethanol step by step, and defated with acetone. The tissue was then placed in a centrifugal tube and embedded with MMA resin at 40° C. After 7–10 days polymerization, the centrifugal tube was removed and the embedded tissues were sectioned by low-speed section machine. The sections were pasted on the slides with Entellan (Merck) and abraded by water abrasive papers until the tissues were pervious to light. The osteoid and calcific bone were differentiated by Von Kossa'a staining, and the healing status of the bone was observed. Finally, the tissues were covered by cover slips with Entellan.

Figure 14:
FIG. 14 is a microscopic photograph showing the Von Kossa's staining result of the healing status of the bioreactor-cultured scaffold after 3 month implantation.
Figure 15:
FIG. 15 is a microscopic photograph showing the Von Kossa's staining result of the healing status of the petri dish-cultured scaffold after 3 month implantation.

Comparing FIG. 14 and FIG. 15, the implanted scaffold cultured in the bioreactor was filled with new osteocytes after 3 months, while the implanted scaffold cultured in the petri dish was only half-filled and a large range of the damaged area was still not healed. The comparison of FIG. 14 and FIG. 15 shows that the scaffold cultured in the bioreactor revealed better osteogenesis than that cultured in the petri dish.

While the invention has been particularly shown and described with the reference to the preferred embodiment thereof, it will be understood by those skilled in the art that various changes in form and details may be made without departing from the spirit and scope of the invention.

What is claimed is:

1. A method for preparing and culturing of cells, comprising the steps of:
   (a) preparing a container with a scaffold;
   (b) placing cell suspension into the container to distribute cells onto the scaffold;
   (c) connecting the container to a reservoir to drive medium into the container; and
   (d) promoting up-and-down medium level motion for cultivation;
       wherein step(a) further comprises a step of settling an oxygenator composed or porous materials above the scaffold to perform aeration during step(d),
       wherein the medium level motion comprises driving the medium level down to expose the oxygenator to the air for aeration, and driving the medium level up to cover the oxygenator by the medium.

2. The method as claimed in claim 1, wherein the container includes a hole for introducing cell suspension.

3. The method as claimed in claim 2, wherein the container is a syringe.

4. The method as claimed in claim 3, wherein the container is single, dual or multiple.

5. The method as claimed in claim 3, further comprising a step (b') between step (b) and (c), placing the syringe for a fixed period to attach cells on the scaffold.

6. The method as claimed in claim 1, wherein the scaffold is composed of porous materials.

7. The method as claimed in claim 1, wherein the scaffold is composed of porous biomedical materials, biodegradable porous high-molecular materials, ceramics, fibers, non-woven or woven sheets.

8. The method as claimed in claim 1, wherein the scaffold is composed of collagen or its copolymers, ceramics, PLGA, PP, PS, PET, hydrophilic polyurethane, polyester, polyvinyl acetate blends, polyvinylidene chloride, polybutadiene, polyfluorocarbons.

9. An apparatus for preparing cells, comprising
   at least one syringe;
   a needle, connected to the base of the syringe;
   a scaffold, placed inside the syringe;
   a push rod, including an end for moving;
   a piston, connected to the end of the syringe; and
   an oxygenator composed of porous material, settled between the piston and the scaffold inside the syringe.

10. The apparatus for preparing cells as claimed in claim 9, wherein the piston is separable to the end of the push rod and comprises a ventilator for ventilation when the push rod separates from the piston.

11. The apparatus for preparing cells as claimed in claim 10, wherein the piston is connected to the end of the push rod by thread.

12. The apparatus for preparing cells as claimed in claim 10, further comprising an air filter, settled on the ventilator to filter microbes out.

13. The apparatus for preparing cells as claimed in claim 9, wherein the scaffold is porous biomedical material, biodegradable porous high-molecular material, ceramics, fibers, non-woven sheets or woven sheets.

14. The apparatus for preparing cells as claimed in claim 9, wherein the scaffold is composed of collagen or its copolymers, ceramics, PLGA PP, PS, PET, hydrophilic polyurethane, polyester, polyvinyl acetate blends, polyvinylidene chloride, polybutadiene, polyfluorocarbons.

15. An apparatus for culturing cells, comprising
   a container;
   a scaffold, sited inside the container;
   a reservoir, reserving a medium and connected to the container for introducing medium into the container;
   a device for liquid driving, moving the medium level up and down; and
   an oxygenator composed of porous materials, sited above the scaffold inside the container to perform aeration during the liquid level movement.

16. The apparatus for culturing cells as claimed in claim 15, wherein the container includes a hole for introducing the medium.

17. The apparatus for culturing cells as claimed in claim 16, wherein the container is a syringe.

18. The apparatus for culturing cells as claimed in claim 17, wherein the container is single, dual or multiple.

19. The apparatus for culturing cells as claimed in claim 17, wherein the device for liquid driving comprises:
   an air pump, used for producing air pressure;
   a solenoid valve, connected to the air pump and the container, comprising two operation modes;
       the first operation mode comprises the steps of pressing air produced by the air pump into the reservoir through the solenoid valve to introduce the medium from the reservoir to the container and raising the liquid level in the container, and the second operation mode comprises the steps of cutting down the air produced from the air pump and decreasing the liquid level in the syringe container;

a controller, connected to the solenoid valve and used for switching the solenoid valve between the first and the second modes in a fixed time interval.

20. The apparatus for culturing cells as claimed in claim 15, wherein the scaffold is composed of porous materials.

21. The apparatus for culturing cells as claimed in claim 17, wherein the device for liquid driving comprises:
a holder, supporting the syringe container;
a power plant, moving the syringe container up-and-down and then moving the liquid level up-and-down.

22. The apparatus for culturing cells as claimed in claim 21, wherein the power plant is a motor.

23. The apparatus for culturing cells as claimed in claim 21, wherein the power plant is a hydraulic cylinder.

24. The apparatus for culturing cells as claimed in claim 21, wherein the power plant is an air cylinder.

25. The apparatus for culturing cells as claimed in claim 15, wherein the device for liquid driving comprises:
a first sensor, sited on the top of the container;
a second sensor, sited under the first sensor with a fixed distance;
an air pump, producing air pressure;
an solenoid valve, connecting the air pump and the container;
a controller, connecting to the first sensor, the second sensor, and the solenoid valve, wherein
when the second sensor detects the medium level, the controller switches the solenoid valve to press air produced by the air pump into the reservoir and the medium of the reservoir pours into the container to raise the medium level in the container;
when the first sensor detects the medium level, the controller switches the solenoid valve to cut down the air produced by the air pump and decrease the medium level.

26. An apparatus for preparing and culturing cells comprising:
a syringe container, withdrawing cell suspension;
a scaffold, sited in the syringe container to distribute cells onto the scaffold when the syringe container withdraws cell suspension;
a reservoir containing a medium, connected to the container to introduce the medium into the container;
a device for liquid driving, promoting up-and-down liquid movement in the container to culture cells; and
an oxygenator composed of porous materials, sited above the scaffold inside the syringe container to perform aeration during the liquid level movement.

* * * * *